(12) United States Patent  
Cramer et al.

(10) Patent No.: US 8,708,987 B2
(45) Date of Patent: Apr. 29, 2014

(54) OSTOMY APPLIANCE WITH MOLDABLE ADHESIVE

(75) Inventors: Kathryn Cramer, Manasquan, NJ (US); George Fattman, Mount Laurel, NJ (US); Tinh Nguyen-DeMary, Milltown, NJ (US)

(73) Assignee: Convatec Technologies Inc., Las Vegas, NV (US)

( * ) Notice: Subject to any disclaimer, the term of this patent is extended or adjusted under 35 U.S.C. 154(b) by 0 days.

(21) Appl. No.: 13/123,926

(22) PCT Filed: Nov. 30, 2009

(86) PCT No.: PCT/US2009/066112
§ 371 (c)(1),
(2), (4) Date: Apr. 13, 2011

(87) PCT Pub. No.: WO2010/060116
PCT Pub. Date: May 27, 2010

(65) Prior Publication Data
US 2011/0213322 A1 Sep. 1, 2011

Related U.S. Application Data

(60) Provisional application No. 61/116,179, filed on Nov. 19, 2008.

(51) Int. Cl.
*A61F 5/44* (2006.01)
(52) U.S. Cl.
USPC ........................................................ 604/344
(58) Field of Classification Search
USPC ........................................................ 604/344
See application file for complete search history.

(56) References Cited

U.S. PATENT DOCUMENTS

| | | | | |
|---|---|---|---|---|
| 4,211,224 A | * | 7/1980 | Kubach et al. | 604/333 |
| 4,367,732 A | * | 1/1983 | Poulsen et al. | 602/56 |
| 4,534,768 A | * | 8/1985 | Osburn et al. | 604/350 |
| 4,701,169 A | * | 10/1987 | Steer | 604/344 |
| 5,545,154 A | * | 8/1996 | Oberholtzer | 604/336 |
| 5,976,118 A | * | 11/1999 | Steer | 604/332 |
| 6,106,507 A | * | 8/2000 | Botten et al. | 604/338 |
| 6,165,159 A | * | 12/2000 | Blanton | 604/333 |
| 6,332,879 B1 | * | 12/2001 | Nielsen et al. | 604/344 |
| 6,709,421 B1 | * | 3/2004 | Falconer | 604/335 |

(Continued)

FOREIGN PATENT DOCUMENTS

| | | | | |
|---|---|---|---|---|
| WO | WO2005048891 | * | 6/2005 | A61F 5/445 |
| WO | WO2007128320 | * | 11/2007 | C08G 77/46 |
| WO | WO2008124717 | * | 10/2008 | A61F 13/66 |

*Primary Examiner* — Susan Su
*Assistant Examiner* — Guy K Townsend
(74) *Attorney, Agent, or Firm* — Wilson, Sonsini, Goodrich & Rosati

(57) ABSTRACT

A body fitment for an ostomy appliance comprises an adhesive wafer including a moldable region shapable by the user. A removable release liner covering an external adhesive surface of the wafer is configured to permit molding of the moldable region by manually manipulating the adhesive through the release liner, and/or with removable segments. In an alternative form, an interior release liner is removable through the entrance aperture of the wafer, by pulling on a grip portion that protrudes through the entrance aperture. In an alternative form, an ostomy pouch includes a finger pocket in a front pouch wall, for permitting insertion of a finger tip for molding the moldable region of an adhesive wafer that is secured around a stomal aperture in a rear pouch wall.

11 Claims, 15 Drawing Sheets

(56) References Cited

U.S. PATENT DOCUMENTS

| | | | |
|---|---|---|---|
| 6,746,765 B1* | 6/2004 | Fattman | 428/355 N |
| 6,764,474 B2* | 7/2004 | Nielsen et al. | 604/344 |
| 6,840,924 B2 | 1/2005 | Buglino | |
| 7,090,664 B2* | 8/2006 | Holter | 604/332 |
| 7,160,275 B2* | 1/2007 | Falconer | 604/333 |
| 7,214,217 B2* | 5/2007 | Pedersen et al. | 604/333 |
| 7,259,190 B2* | 8/2007 | Lykke | 521/146 |
| 2003/0004477 A1* | 1/2003 | Nielsen et al. | 604/336 |
| 2004/0065232 A1* | 4/2004 | Lykke | 106/680 |
| 2004/0193122 A1* | 9/2004 | Cline et al. | 604/332 |
| 2005/0015065 A1* | 1/2005 | Falconer | 604/335 |
| 2005/0054997 A1* | 3/2005 | Buglino et al. | 604/332 |
| 2005/0065486 A1* | 3/2005 | Fattman | 604/332 |
| 2005/0075616 A1* | 4/2005 | Holter | 604/332 |
| 2005/0282977 A1* | 12/2005 | Stempel et al. | 525/477 |
| 2006/0184145 A1* | 8/2006 | Ciok et al. | 604/338 |
| 2007/0027434 A1* | 2/2007 | Pedersen et al. | 604/333 |
| 2007/0123832 A1* | 5/2007 | Cline et al. | 604/335 |
| 2007/0185464 A1* | 8/2007 | Fattman et al. | 604/336 |
| 2009/0148661 A1* | 6/2009 | Stroebech et al. | 428/137 |
| 2009/0149567 A1* | 6/2009 | Lam et al. | 523/111 |
| 2009/0216169 A1* | 8/2009 | Hansen et al. | 602/48 |
| 2009/0306571 A1* | 12/2009 | Lam et al. | 602/56 |
| 2010/0016820 A1* | 1/2010 | Lam et al. | 604/344 |
| 2010/0113999 A1* | 5/2010 | Lam et al. | 602/79 |
| 2010/0191201 A1* | 7/2010 | Bach et al. | 604/336 |
| 2010/0191204 A1* | 7/2010 | Bach et al. | 604/344 |
| 2010/0198176 A1* | 8/2010 | Stroebech et al. | 604/344 |
| 2010/0204664 A1* | 8/2010 | Bach et al. | 604/344 |
| 2010/0204665 A1* | 8/2010 | Stroebech et al. | 604/344 |
| 2011/0125115 A1* | 5/2011 | Anders et al. | 604/344 |

* cited by examiner

OSTOMY APPLIANCE WITH MOLDABLE ADHESIVE

FIELD OF THE INVENTION

The present invention relates to an ostomy appliance with a moldable adhesive. In one form, the invention relates to a body fitment including a peristomal adhesive wafer. In another form, the invention relates to a so-called one-piece appliance in which an adhesive wafer is permanently attached to the appliance, although the invention may also be used with a two-piece appliance in which the adhesive wafer is releasably attachable to the appliance.

BACKGROUND TO THE INVENTION

Modern ostomy appliances are commonly attached to the body by means of an adhesive wafer, having an opening for the stoma sometimes referred to as a starter hole. The adhesive is laminated between plastics films. The film on one side acts a release liner that is removed by the user prior to fitting to the skin. The film on the other face remains permanently in place to prevent the wafer adhering undesirably to the interior of the appliance. The films are sufficiently stiff to stabilize the shape of the wafer, and to protect the adhesive surface that will, in use, contact the skin.

Ostomy appliances commonly fall into two types, called one-piece and two-piece appliances. In a two-piece appliance, the adhesive wafer forms part of a separate body fitment component that is attached by a releasable coupling. A two-piece appliance permits the body fitment to be separated from the appliance without damage, so that at least one of the components continues to be functionally usable. For example, the body fitment may remain in place on the body, and a replacement pouch appliance mounted in place of a used pouch appliance. Two-piece appliances are preferred by some users as they involve less frequent removal the adhesive wafer, which may be used with several different appliances. In contrast, in a one-piece appliance, the adhesive wafer is permanently attached to the appliance, to the extent that the adhesive wafer cannot easily be separated without risk of damaging the appliance. A one-piece appliance is intended to be used as an integral unit. One-piece appliances are preferred over two-piece appliances by some users for a variety of reasons. The absence of the releasable coupling means that their overall profile on the body is reduced, increasing discretion of the appliance. They are generally more flexible than two-piece appliances. They are also simpler to teach and learn than two-piece appliances, and can be more convenient as a result of the need to keep fewer products available for use. Finally, they are sometimes preferred for hygienic reasons since they tend to be more disposable and so may be changed more frequently.

For both one-piece and two-piece appliance types, proper fit of the wafer around the stoma is critical to proper functioning of the wafer, but can be problematic because most commercially available wafers are not manufactured to the identical size, or shape, of an individual's stoma. The wafer must be modified in some way to adapt it to the stoma, and the modification most frequently performed is to manually cut the wafer opening to try to match the size and shape of the stoma. The starter hole gives the wearer a place to start cutting using scissors. In one form, the edge of the wafer opening should be no more than approximately 0.125 inches from the stoma around its entire periphery, for optimum fitting of the appliance. It is difficult to obtain a cut of such precision, because of the aggressive nature of the adhesive against the scissors, and the compliance of the wafer. An even more precise match around the stoma would be preferable, but of course is even more difficult to achieve.

As mentioned above, the degree of matching of the wafer opening to the stoma shape and size is critical to proper functioning of the wafer. As well as attaching the appliance to the skin, the wafer also protects the peristomal skin from contact by stomal effluent. Protection of peristomal skin is important because effluent in contact with the skin causes rapid and severe skin break down. Stomal effluent contains digestive juices that cause excoriation of skin tissue. In addition to being painful, denuded skin is poorly suited to attachment of subsequent wafers, leading to a degenerative cycle of poor attachment, reduced skin protection, and further worsening of the skin condition. Critical elements of skin protection include secure leak-proof adhesion to peristomal skin, and a proper fit of the wafer around the stoma itself. More specifically with respect to fit, it is critical to closely match the wafer opening to the stoma periphery. If the match is imprecise, then skin will be exposed and vulnerable to attack by effluent.

U.S. Pat. No. 6,840,924 describes an improved ostomy appliance including a moldable adhesive, in which at least a portion of the adhesive can be manually molded by the wearer, to provide a custom fit around the stoma. This alternative way of customizing the wafer offers the prospect of a better fit around the stoma than that obtainable by cutting. The adhesive surface of the wafer is exposed on the non-body-facing side, allowing the rim of the adhesive to be rolled or folded back into adhesive contact with itself on the non-body-facing side to anchor the adhesive in its newly molded shape. The moldable adhesive is described for use in both one-piece and two-piece appliances.

However, the absence of film on the non-body facing side of a moldable wafer prevents more of a problem for a one-piece appliance. This occurs because the adhesive would adhere to the interior of the pouch.

If a non-body side wafer surface of a one-piece pouch has a protective film liner, this appliance has additional problems. The presence of, for example, a pouch permanently attached on the non-body-facing side of the wafer obstructs access to the non-body-facing side for removing the protective film to expose the adhesive surface on the non-body-facing side. Without the film, the adhesive may be vulnerable to adhering undesirably to the pouch wall opposite the wafer. Moreover, the presence of the release liner on the body-facing side of the wafer hinders deformation of the wafer, thereby obstructing moldability. Worse still, the release liner hinders finger access through the starter opening for folding or rolling back the adhesive around the starter opening for shaping the opening. A common size of stoma is 25 mm diameter, and for such a size the starter opening should be slightly smaller. However, if the starter opening is less than 25 mm, it is difficult to comfortably or effectively insert a finger through the starter opening for freely molding the wafer.

In general, it is preferred not to remove the release liner until the final moment prior to adhering the wafer to the peristomal skin. The release liner has an important function in protecting the adhesive from contamination, for example, by skin oils or other contaminants that reduce adhesion strength. The effectiveness of the wafer to adhere optimally to skin, and to protect the skin from attack by stomal effluent, depends to a large extent on the wafer not having been exposed substantially prior to contacting the peristomal skin.

Additionally, the presence of a properly designed release liner can act as a molding tool or aid by providing a surface against which the molding process can be effectively conducted as it offers better control of the final dimensions and shape of the wafer.

The present invention provides surprising solutions to these problems.

SUMMARY OF THE INVENTION

Broadly speaking, one aspect of the present invention provides an adhesive wafer for attaching an ostomy appliance to a wearer's body. The adhesive wafer includes a moldable region for allowing a user to manually mold a stomal aperture in the moldable region. A release liner protects at least a portion of an adhesive surface of the moldable region of the adhesive. The release liner is configured to allow molding of the moldable region, by manipulating the adhesive through the release liner, either through the starter hole or by pressing the release liner against the adhesive while the release liner remains partially or entirely in contact with the adhesive surface. A further aspect of the invention is that a release liner on the inside of the pouch protecting the moldable region of the adhesive wafer is designed to be removable through an aperture in the appliance.

The term "release liner" refers to any device or member that is attached to line at least a portion of an adhesive surface of the wafer, but is made of or coated with a material (for example, silicone) to which the adhesive surface adheres relatively weakly, so that the release liner may be removed easily from the adhesive without substantially distorting the adhesive shape. The term "release liner" also includes sheets of material designed with surface features, such as embossing or other surface features resulting in a texture or roughness or other surface discontinuity that reduces contact between such sheet and adhesive surface so as to facilitate separation between the adhesive and sheet surface. Release liners of this design may also be useful for protection of adhesive surfaces in ostomy, wound care and incontinence devices. This release liner is particularly effective where the adhesive contact side is coated with an adhesive reducing material such as silicone.

A release liner configured according to this aspect of the present invention offers significant advantages by enabling the molded region of the adhesive to be molded from the side on which the release liner is attached. This can prevent the user's fingers from sticking to, or becoming tacky as a result of contact with, the adhesive during molding. The nature of the adhesive means that the adhesive is especially configured to adhere to skin, and so any reduction in direct contact between the user's finger and the adhesive is an advantage. It can also protect the adhesive against contamination, by, for example, any one or more of dirt, bacteria, grease, skin oils, and/or or moisture that may be on the skin of the user's finger, and would be desirable not to transfer onto the surface of the adhesive. The release liner also does not need to be removed early before molding the adhesive, thereby enabling the release liner to protect the adhesive surface until the release liner is removed just prior to adhering the body fitment to the body.

The release liner may be on the body-facing side of the adhesive, thus permitting molding from the body-facing side. The release liner may be on the non-body-facing side, thus permitting molding from the non-body-facing side. Release liners according to the invention may also be provided on both the body-facing side and the non-body-facing side of the adhesive, if desired.

In one form, the release liner presents a substantially continuous surface extending over the face of at least the moldable region of adhesive, even when the adhesive is being molded. If the adhesive includes a starter hole, the release liner may optionally extend across the starter hole as well as over the adhesive face, or the release liner may include an aperture in register or co-located with the starter hole. The aperture in the release liner may be of about the same size as the starter hole (simplifying manufacture by making it easy to punch the starter hole through a laminate of both the adhesive wafer and the release liner as a unit), or the aperture may be larger or smaller than the starter hole.

The release liner may be made of a flexible or stretchable material, so that the release liner can conform to the molded shape of the adhesive. Additionally or alternatively, the release liner may incorporate a flexible protrusion (or "finger pocket") into which the user may insert at least the tip of a finger, to mold the adhesive while avoiding direct contact between the finger and the adhesive. The flexible protrusion may be shaped as an elongate tube.

Additionally or alternatively, the release liner may have one or more division lines that permit at least partial separation of zones of the liner, to reduce the extent to which the liner restrains moldability. The division lines may include one or more cuts or slits, and/or one or more lines of weakness. The lines of weakness that allow the release liner to break once the release liner is deformed beyond a certain point or is subjected to a stress beyond a certain threshold.

In a second aspect, the invention provides a removable release liner covering at least a portion of an adhesive surface of the moldable region of the adhesive wafer. The release liner may comprise at least one division line dividing the release liner into a plurality of segments. At least one of the segments overlaps the moldable region of the adhesive. The division line may permit at least one segment of the release liner to be selectively removed either partially or entirely from the adhesive surface while another segment remains in adhesive contact, whereby the removed segment permits molding of the moldable region unrestrained by the removed release liner segment.

In a third aspect, the invention provides an interior release liner substantially covering a non-body-contacting face of a moldable region of an adhesive wafer. The release liner including a grip portion for enabling the interior release liner to be removed from the non-body-contacting face of the adhesive wafer, to facilitate molding of the moldable region.

The release liner prevents undesired adhesion between the adhesive non-body-contacting face of the adhesive, and the interior of the pouch that is opposite the non-body-contacting face of the adhesive at the entrance aperture or at the moldable region of the wafer.

The grip portion may extend through or towards an aperture of the appliance, to enable manipulation by a user. The aperture may, for example, be the starter hole of the adhesive wafer, or a drainage aperture. Preferably, the release liner is configured to be removable from the pouch interior by being pulled out through the aperture.

The grip portion is preferably configured to promote peeling of the interior release liner, for example, by including a suitable fold. The interior liner may optionally include a division line that divides the area of the liner into at least one continuous segment or strip that can be pulled progressively through the aperture in elongate form, to remove the liner. The division line may, for example, be of a spiral form.

Alternatively, a plurality of division lines may be used to effect a collapse or folding in the structure of a release liner causing its size to be reduced so as to facilitate its removal through an aperture in the appliance. For example, the liner shape may be in the form of a collapsing cone with a plurality of division lines causing the cone to collapse with a mechanism similar to folding an umbrella.

In a fourth aspect, the invention provides a release liner for protecting the non-body-contacting face of the adhesive wafer to obstruct adhesion of the non-body-contacting face to the front wall of the pouch in a region opposite the entrance aperture or moldable region, the release liner being secured to the front wall of the pouch.

In a fifth aspect, the invention provides an ostomy appliance with a finger pocket made of flexible material, the finger pocket being dimensioned to enable a user to insert at least a tip of a finger into the pocket, and the finger pocket being disposed to enable the user to mold at least a part of an adhesive wafer by means of the fingertip inserted into the pocket. The finger pocket is open at a first end. A second end may be closed.

The finger pocket can (i) provide access to a region of the adhesive for molding, where access is otherwise obstructed by the appliance, and/or (ii) provide a protective sheath that to prevent the adhesive from sticking to the user's finger, and to prevent contamination of the adhesive by direct contact with the finger.

In one form, the finger pocket is disposed to extend adjacent to, or opposite, a stomal aperture of the appliance. The finger pocket may be formed in a wall of a ostomy pouch, for example, the front wall or the rear wall. In another form, the finger pocket is provided as a part of a removable release liner protecting a portion of the adhesive wafer that is exposed in use of the appliance (such as a face and/or edge portion of the adhesive wafer). The finger pocket may be integral with the remainder of the release liner, or it may a separate release liner component.

Viewed in a further aspect, a body fitment for an ostomy appliance comprises an adhesive wafer including a moldable region shapable by the user. In one form, a removable release liner covering an adhesive surface of the wafer is configured to permit molding of the moldable region by manually manipulating the adhesive through the release liner, while the release liner remains in situ. The release liner may include stretchable material and/or one or more breakable regions and/or a finger pocket, to permit manual molding of the adhesive. In an alternative form, an ostomy pouch includes a finger pocket in a front pouch wall, for permitting insertion of a finger tip for molding the moldable region of an adhesive wafer that is secured around a stomal aperture in a rear pouch wall.

The above aspects may be used independently of each other or in any combination of two or more of these aspects.

While features believed to be of special significance have been identified above and the appended claims, claim protection may be sought for any novel feature or idea described herein and/or illustrated in the drawings, whether or not emphasis has been placed thereon.

DETAILED DESCRIPTION OF THE PREFERRED EMBODIMENTS

Figure 1:
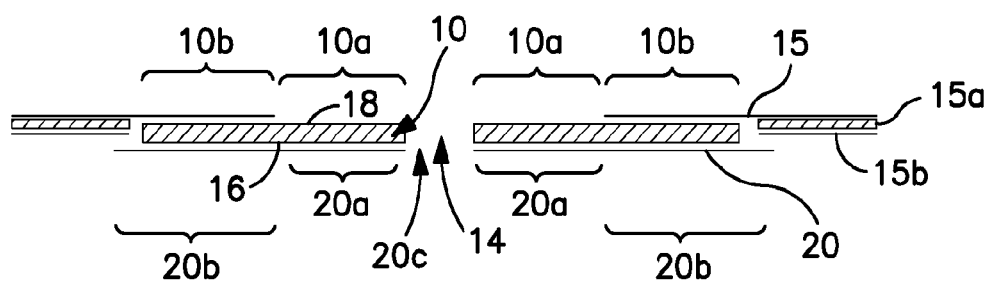
FIG. 1 is a schematic cross-sectional view through a first embodiment of body fitment for an ostomy appliance, including a stretchable release liner.
Figure 2:
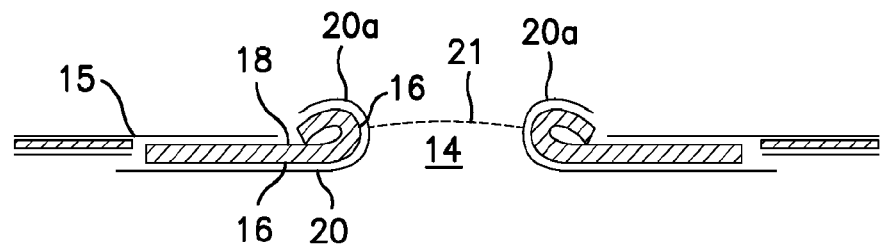
FIG. 2 is a schematic cross-sectional view similar to FIG. 1, showing molding of the first embodiment.

Referring to FIGS. 1 and 2 a first embodiment illustrates an adhesive wafer 10 for use as a body fitment for an ostomy appliance (50/54 in FIG. 7 or 8 described later). The adhesive wafer 10 comprises skin compatible adhesive intended to adhere to peristomal skin and/or form a peristomal seal. At least a portion 10a of the wafer 10 around a stomal aperture or starter hole 14 is configured to be moldable or shapable to enable the user or a caregiver to customize the shape of the stomal aperture 14 by manually molding the adhesive portion 10a. Initially, the adhesive wafer 10 may have no stomal aperture 14, so that a user creates the aperture 14 by molding or other means, or the adhesive wafer 10 may include a starter hole 14 that is subsequently shaped (for example, enlarged) by manual molding of the moldable region 10a.

The adhesive wafer 10 may be a primary weight bearer for supporting the weight of a pouch by adhesive engagement with the skin. The adhesive wafer 10 may, for example, be of the type taught in the aforementioned U.S. Pat. No. 6,840, 924. The adhesive may define a laminate structure. The laminate structure includes plural layers of adhesive and/or at least one layer of adhesive and at least one flexible sheet. Alternatively, the moldable region 10a may be of a putty-like or flowable adhesive.

The moldable portion 10a may be surrounded by a substantially non-moldable (or at least less moldable) region 10b. The moldable and non-moldable regions 10a and 10b may be integral with each other, and distinguished by an optional backing 15 that restricts moldability of the region 10b. In the illustrated form, the backing 15 is defined by a microporous sheet that extends optionally beyond the outer periphery of the adhesive wafer 10 (as may be seen in the views of FIGS. 3 and 4), and carries a second skin-friendly adhesive 15a, at least in the region extending outside the periphery of the adhesive wafer 10. Alternatively, the backing 15 may be a foam member (not shown) that interfaces between a pouch and the adhesive wafer 10.

In the example shown, the wafer 10 may be generally circular, and the backing 15 may be generally rectangular with rounded corners. However, such shapes are not limiting. Any suitable shape of wafer 10 and/or backing 15 may be used as desired.

The adhesive wafer 10 has a body-contacting face 16 for contacting the wearer, when fitted to the body. The adhesive wafer 10 also has a non-body-contacting face 18 opposite the body-contacting face 16. A release liner 20 is initially provided covering at least a portion of at least one of these faces, for example, the body-contacting face 16, to prevent the adhesive wafer 10 accidentally adhering to the other components of the ostomy appliance 12 when packaged together, and/or to protect the adhesive face 16 to preserve its adhesive properties. The release liner 20 covering the body-contacting face 16 may be referred to as an external release liner. The release liner 20 typically comprises plastic film coated with silicone, such that the adhesive wafer 10 adheres only weakly to the release liner 20, enabling the release liner 20 to be peeled away when desired without substantially deforming the adhesive wafer shape. In the form illustrated, the release liner 20 is slightly larger than the adhesive wafer 10 around the entire periphery of the wafer 10 (also visible in FIGS. 3 and 4), so that a user may grip the release liner 20 at any position around its edge to begin peeling the release liner 20 away. In an alternative form, the release liner 20 may be of about the same size as the adhesive wafer 10, and be provided with one or more laterally extending tabs (not shown) by which the release liner 20 may be gripped.

The release liner 20 is configured to allow molding of the moldable region 10a of the adhesive wafer 10, by manipulating the adhesive through the release liner 20, while the release liner 20 remains in contact with the adhesive surface, such as body-contacting face 16. This feature (i) avoids direct contact between the finger or fingers of the person molding the adhesive, and significant area of the adhesive surface itself, and (ii) avoids having to remove the release liner 20 early to perform the molding. Avoiding direct contact with significant area of the adhesive is beneficial, otherwise the adhesive might stick to the user's fingers, leaving the fingers tacky, or the adhesive surface might become contaminated with dirt, bacteria, grease and/or body oil from the user's fingers. Avoiding early removal of the release liner 20 is further advantageous in enabling the adhesive surface to be protected for as long as possible prior to attachment to peristomal skin.

In the present embodiment, at least a first portion 20a of the release liner 20 is made of stretchable material. The term "stretchable" means that the release liner 20 can be extended beyond its unrestrained dimensions without breaking by applying digital manipulation. The extent of the strain induced may be fully or only partially recoverable upon discontinuation of manipulation. The portion 20a may be at least partly resiliently stretchable and/or at least partly plastically stretchable. The portion 20a extends under the moldable region 10a of the adhesive wafer 10. In the form illustrated, the adhesive wafer 10 includes a starter hole 14, and the portion 20a includes an aperture 20c in register with the starter hole 14. The aperture 20c may be of the same size and shape as the starter hole 14. This simplifies manufacture by enabling the adhesive wafer 10 and the release liner 20 to be formed as a laminate structure, which is then punched as a unitary item to form the body fitment with the starter hole 14 and the aperture 20c. Alternatively, the aperture 20c may be smaller than the starter hole 14 to protect the inner edge of the adhesive during molding, or the aperture 20c could be larger than the starter hole 14. In a further form, the portion 20a may extend continuously over the starter hole 14 to cover the starter hole 14.

The entire release liner 20 may be made of stretchable material, or a portion 20b around the first portion 20a may be made of substantially non-stretchable material. When two different portions 20a, 20b are implemented as an integral release liner 20, the different stretching properties may be provided by different thicknesses of the same material, or by joining together two pieces of different materials to form a unitary release liner 20. Alternatively, the two different portions 20a, 20b may be separate pieces, defining separate, distinct release liner segments. One example is a release liner 20 made of polyethylene film.

FIG. 1 shows the adhesive wafer 10 and release liner 20 together referred to as a body fitment in an initial condition prior to molding of the adhesive. FIG. 2 shows how the portion 20a of stretchable material deforms during molding of the moldable region 10a. Typically, the rim edge of the adhesive surrounding the starter hole 14 is pushed, rolled or folded back towards the non-body-facing side 18, to enlarge and shape the starter hole 14 to a custom form to suit the user's stoma. The folded back portion of the adhesive may adhere to itself on the non-body-facing side 18 to anchor the adhesive in its molded shape. The region 20a of stretchable material allows the molding operation to be carried out by applying finger pressure to manipulate the adhesive at least from the body-facing side 16, and the region 20a deforms to follow at least partly the modified shape of the adhesive, and to allow the user's fingers to mold the desired shape of stomal aperture 14. In the form illustrated in FIG. 2, the first portion 20a stretches such that the first portion 20a remains in contact with substantially the entire body-contacting surface 16 of the adhesive during molding. The stretchable portion 20a may be sufficiently flexible that the stretched shape can easily be withdrawn back through the stomal aperture 14 when the release liner 20 is later peeled away just prior to fitting the adhesive wafer 10 to the body. Alternatively, as illustrated in phantom at 21, the first portion 20a may stretch resiliently during molding, and return elastically towards a retracted shape when the user's finger is removed. The first portion 20a may thus begin to peel away from the region of the adhesive that has been molded by bending back on itself.

The adhesive 15a of the backing 15 may also be protected initially by a second removable release liner 15b intended to be removed prior to, or during, fitting of the adhesive wafer 10 to the body. For example, the second release liner 15b may consist of first and second butterfly-wing segments that can be peeled away separately once the adhesive wafer 10 has been initially adhered around the stoma, to enable the backing 15 subsequently to be adhered to the body. In another form, the release liner 20 may be large enough to cover both the adhesive wafer 10 and the backing 15, so that only a single release liner 20 is used.

Figure 3:
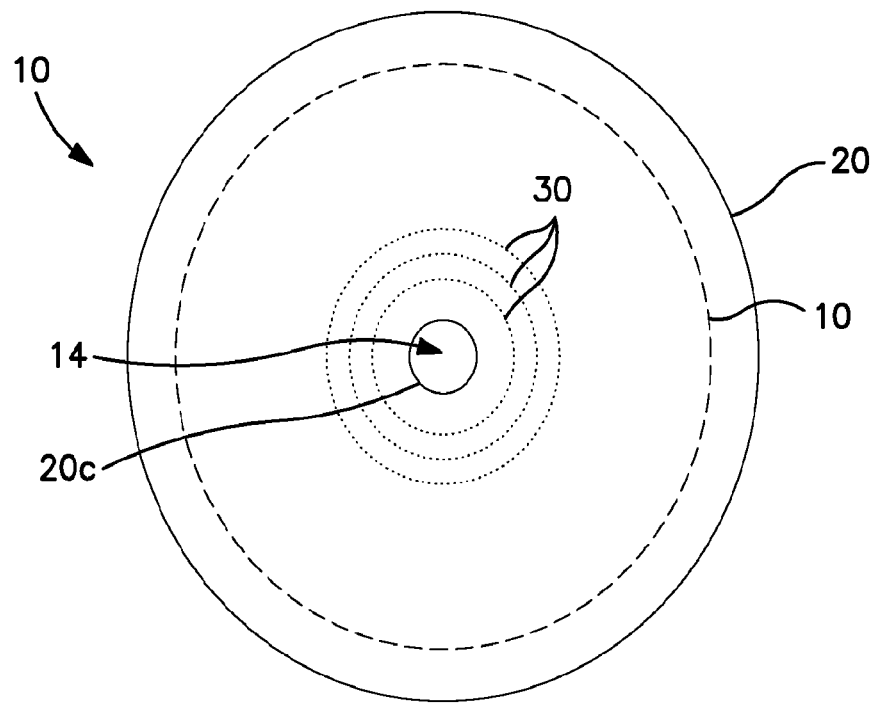
FIG. 3 is a schematic rear view from the body-contacting-side of a second embodiment of body fitment for an ostomy appliance, including a release liner with a division line.
Figure 4:
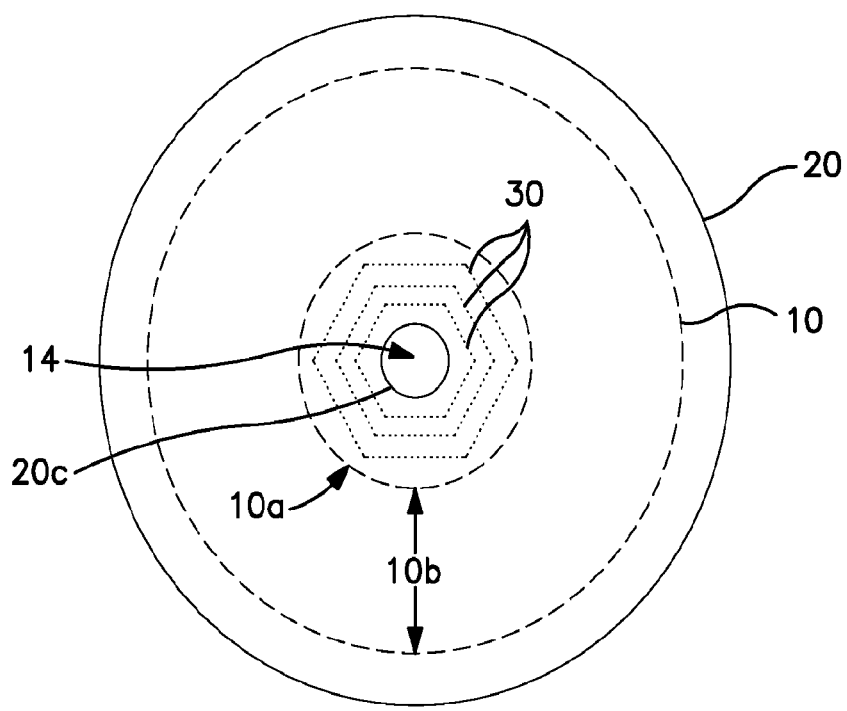
FIG. 4 is a schematic view similar to FIG. 3, showing a modification of the second embodiment.
Figure 5:
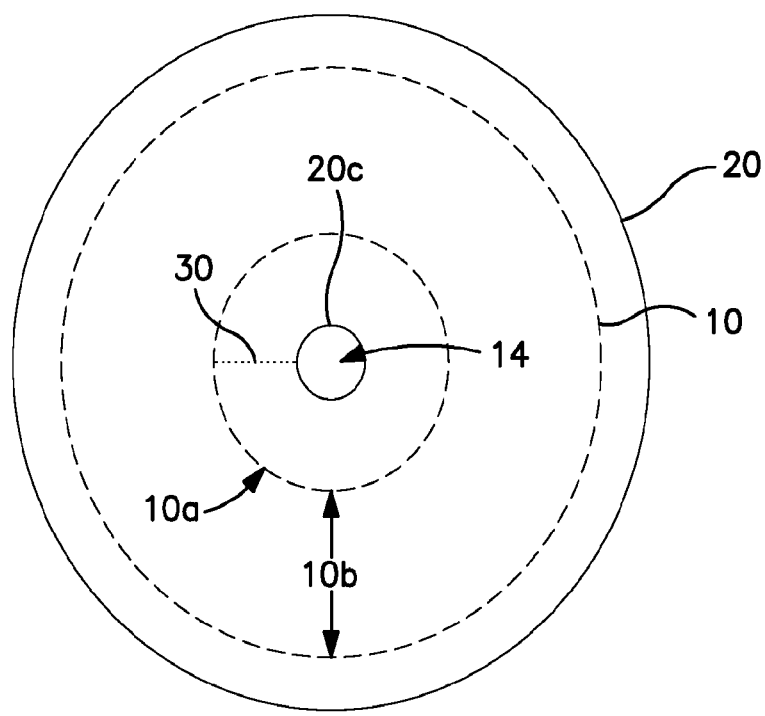
FIG. 5 is a schematic view similar to FIG. 3, showing a further modification of the second embodiment.

FIGS. 3 and 4 illustrate a second embodiment showing an alternative way of implementing the release liner 20. The release liner 20 comprises substantially non-stretchable material, or at least less-stretchable than the first embodiment. At least one division line 30 is defined in the release liner 20 near or adjacent the moldable region 10*a* of the adhesive wafer 10. The division line 30 may be a preformed cut or slit in the release liner 20, or it may be a line of weakening that can tear or flex more easily than the remainder of the release liner 20. The line of weakening 30 may be defined by perforations leaving frangible connections, or by scoring, or other material thinning or dimensional changes. The one or more division lines 30 divide the release liner 20 to define zones that are, or can break, at least partly free, to overcome the release liner 20 restraining the shape of the adhesive wafer 10, and permit molding of the moldable region 10*a*.

Figure 6:
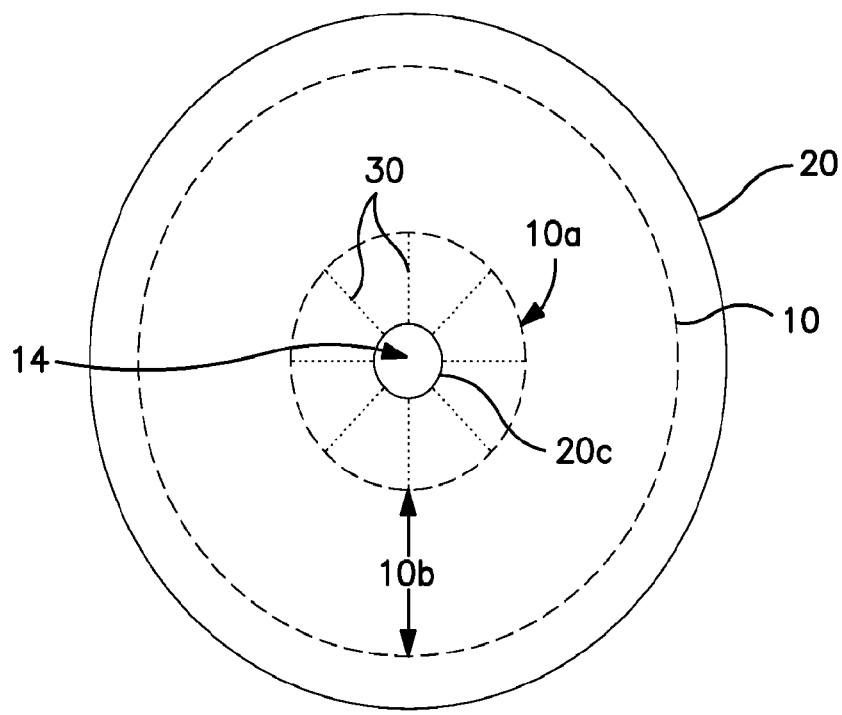
FIG. 6 is a schematic view similar to FIG. 3, showing a further modification of the second embodiment.

As illustrated in FIGS. 3 and 4, the division line 30 may be of closed loop shape, for example, circular as in FIG. 3, or polygonal as in FIG. 4. The division line 30 may optionally have the same shape as the starter hole 14 and/or optionally the general shape of the moldable region 10*a* within the adhesive wafer 10. Additionally or alternatively, as shown in FIGS. 5 to 9, the division line 30 may emanate from the starter hole 14. For example, in FIG. 5, a single division line 30 extends radially from the starter hole 14. In FIG. 6, plural division lines 30 extend radially from the starter hole 14, dividing the material into angular segments (like triangular "cheese" segments) of material under the moldable region 10*a*. For example, six such radial lines may be preferred. In FIG. 7, the division line 30 has a rounded spiral shape, and in FIG. 8 the division line 30 has a polygonal spiral shape. In FIG. 9, the division line 30 includes boustrophedon turns that progress outwardly in the manner of a split spiral.

Figure 10:
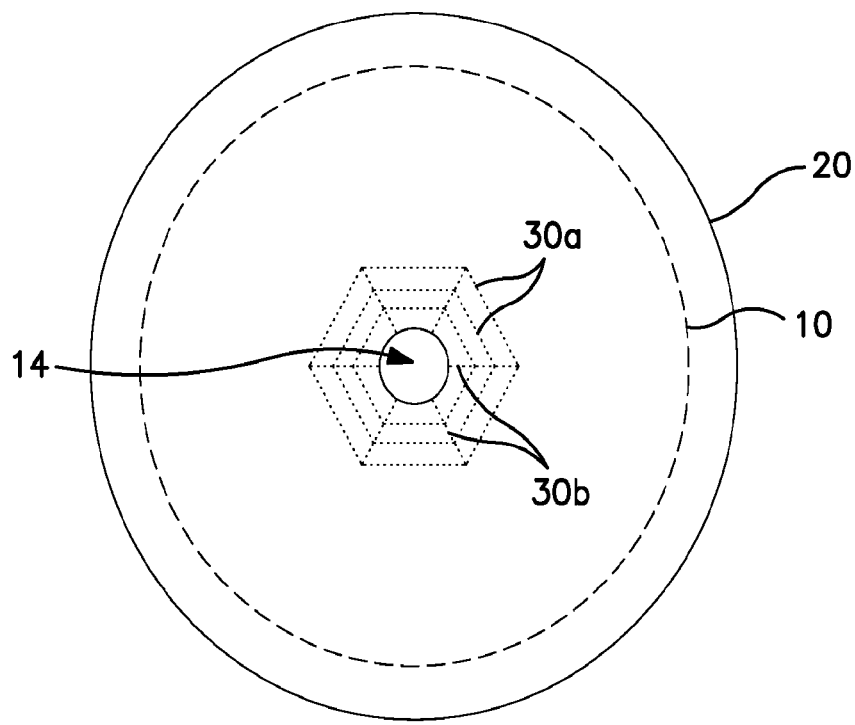
FIG. 10 is a schematic view similar to FIG. 3, showing a further modification of the second embodiment.

Any combination of shapes may also be used as desired. FIG. 10 illustrates a combination of at least one (and optionally plural) closed-loop division line 30*a*, and at least one (and optionally plural) radial division lines 30*b*. The shape may resemble a spider's web.

Two modes of operation are envisaged.

In one mode, a portion of the release liner 20 is intended to be removed manually from the adhesive surface of the wafer 10 in the moldable region 10*a*. The removed portion of the release liner 20 may be separated and discarded, or it may remain attached to the remainder of the release liner 20 but not adhered to the adhesive surface of the wafer 10 in the moldable region 10*a*. The removed portion of the release liner 20 removes the restraining effect of the release liner 20 in the moldable region 10*a* of the adhesive. The moldable region 10*a* may then be shaped as desired by insertion of a finger, while the remainder of the release liner 20 protects and stabilizes the non-moldable region 10*b*. The user may also be able to choose how much of the release liner 20 to remove, based on the user's experience of how much molding of the starter hole 14 is required. If the user only needs to employ a small part of the moldable region 10*a*, the user may decide only to remove the release liner 20 in the area desired to be molded, instead of exposing the entire moldable region 10*a*. Such choice can enable the remainder of the release liner 20 to protect and stabilize even a portion of the moldable region 10*a* that is not intended to be molded.

In an alternative mode, the release liner 20 remains substantially adhered to the surface of the adhesive. The division line 30 relaxes the restraining effect of the release liner 20 to permit molding of the moldable region 10*a* of the adhesive from the body-contacting side 16 without removing the release liner 20. The release liner 20 can therefore continue to protect the area of adhesive that it overlaps, ensuring that these areas can achieve good adherence to skin when the liner is removed for fitting. If the division line 30 is a line of weakening, the point at which breaking occurs depends on the nature of the release liner 20. If the release liner 20 is made of substantially non-stretchable material, one or more lines of weakening 30 may break under stress as soon as the shape of the moldable region 10*a* is changed. If the release liner 20 is made of partly stretchable material, the material may initially stretch to accommodate the change of shape during molding, and one or more lines of weakening 30 may break when the change of shape exceeds the stretchability of the material, or a threshold stress is reached corresponding to the strength of the line of weakening.

In the second mode of operation, even a simple division line 30 (for example, a single radial division line 30 as in FIG. 5) can increase the shapeability of the moldable region 10*a* to a surprisingly significant extent, much greater than would be expected compared to merely increasing the stretchability of the release liner 20 without a division line 30.

Again for the second mode, the optimum type of molding or shaping may depend on the nature and/or flexibility of the release liner 20. This is because the release liner 20 will still have some restraining effect on shapeability in the areas the release liner 20 continues to overlap. For example, it has been found that when the release liner 20 material is less rigid, such as when using polyethylene-co-vinyl acetate film about 0.002 inches thick, manipulation is best accomplished by folding the exposed adhesive to tack it to itself about a single fold. When a more rigid release liner 20 is used, such as a polyester film between about 0.005 and about 0.010 inches thick, the method of adhesive shaping most easily performed is a rolling action. Rolling is preferred because it offers a greater degree of control. The rolling process is easier to target and to some extent undo if needed as compared with a folding process.

Figure 11:
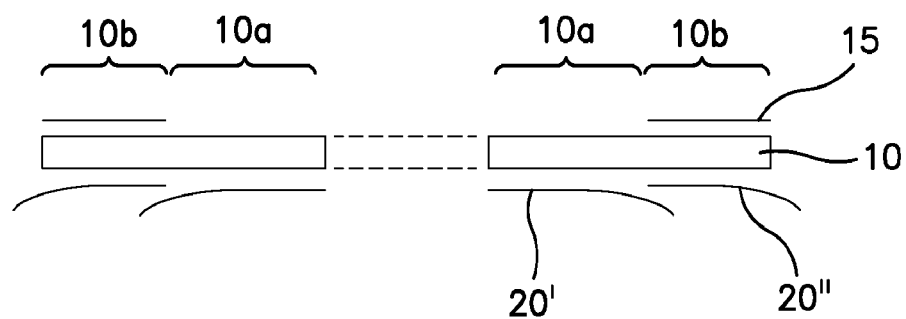
FIG. 11 is a schematic cross section showing a further modification of the second embodiment.

FIG. 11 shows a further modification in which the release liner 20 comprises first and second separate parts 20' and 20". The first part 20' covers the moldable region 10*a*, and the second part 20" covers the non-moldable region 10*b*. Each part may have a respective finger grip area. The parts 20', 20" are concentric or positioned one around the other. Such an arrangement may be more expensive to produce, as the first and second liner parts 20', 20" might not be made from a single piece of material in a single laminate. However, such an embodiment may nevertheless enable the release liner part 20' to be removed independently for molding the moldable region 10*a* of the wafer 10, while leaving the second part 20" in place to stabilize and protect the non-moldable region 10*b*. Although only two parts 20', 20" are illustrated, it will be appreciated that more than two parts may be used as desired, in order to allow the user to choose how much of the adhesive area to expose for molding, in a similar manner as that described above.

Figure 12:
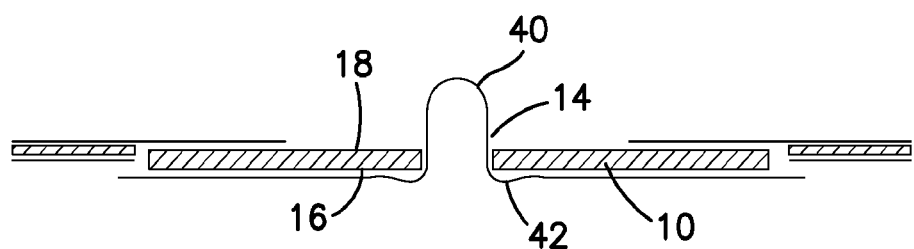
FIG. 12 is a schematic cross-sectional view through a third embodiment of body fitment for an ostomy appliance, including a release liner with a finger pocket.
Figure 13:
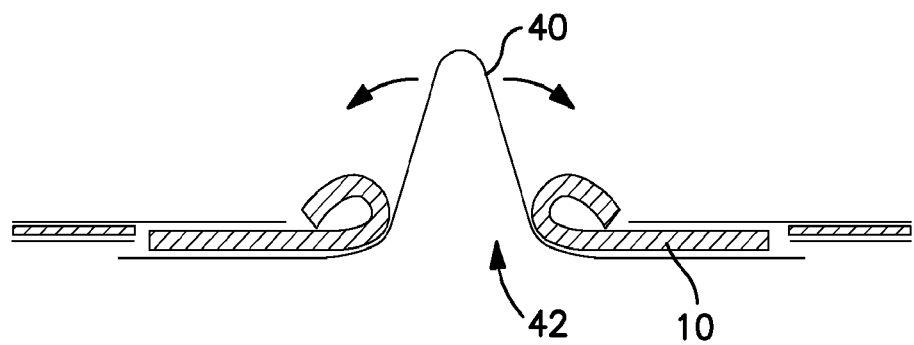
FIG. 13 is a schematic cross-sectional view similar to FIG. 5 showing molding of the third embodiment.

FIGS. 12 and 13 illustrate a third embodiment showing a further alternative way of implementing the release liner 20. A sock, sleeve or protrusion of flexible material defines a finger pocket 40 provided at the stomal aperture 14, for permitting at least the fingertip of a person's finger to be inserted from the body-contacting side 16 for molding the adhesive in the region 10*a* around the stomal aperture 14. The finger pocket 40 may be integral with the remainder of the release liner 20. For example, it may be made of the same material as the remainder of the release liner 20, and shaped for example, by thermo-forming. Alternatively, the finger pocket 40 may be made of different material, and joined to the remainder of the release liner 20 to form a unitary item. As a further alternative, the finger pocket 40 may be a separate component that is distinct from the remainder of the release liner 20. The finger pocket 40 nevertheless has "release" properties, by being made of or coated with a material (such as silicone) for allowing easy separation or peeling from adhesive contact with the adhesive wafer 10, without substantially deforming the shape of the adhesive. Alternatively, the surface of the finger pocket may be textured.

The finger pocket 40 may be made of stretchable material, to permit the finger pocket 40 to expand to follow the enlarged shape of the stomal aperture 14 normally produced by molding. Alternatively, the finger pocket 40 may be oversize, for example, up to the size or outer periphery of the moldable region 10a of the adhesive wafer 10. If implemented oversize, at least the mouth region 42 of the finger pocket 40 is enlarged compared to the initial stomal aperture 14, for example, defining a bell or flared shape. The end of the finger pocket 40 opposite the mouth region 42 is preferably closed, but may be open, if desired.

Figure 14:
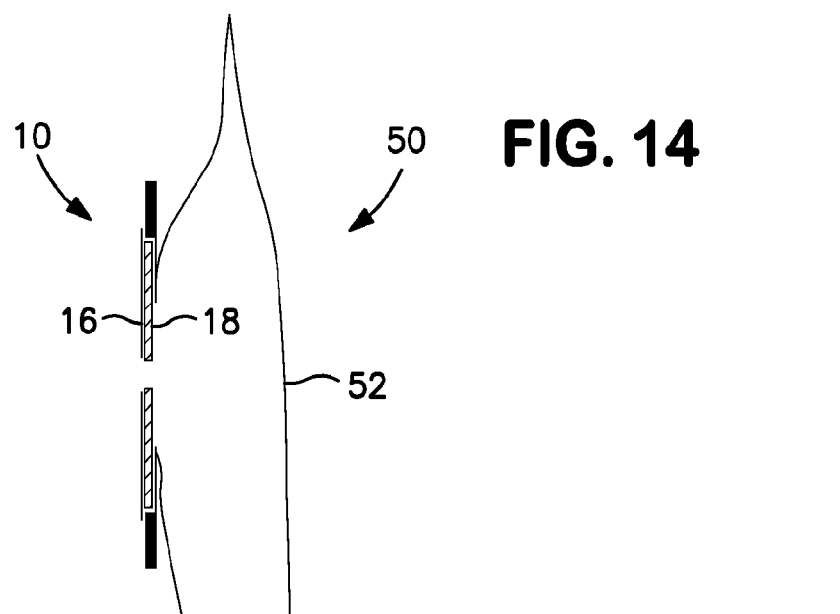
FIG. 14 is a schematic cross-sectional view showing the $1^{st}$-$3^{rd}$ embodiments used with a one-piece appliance.
Figure 15:
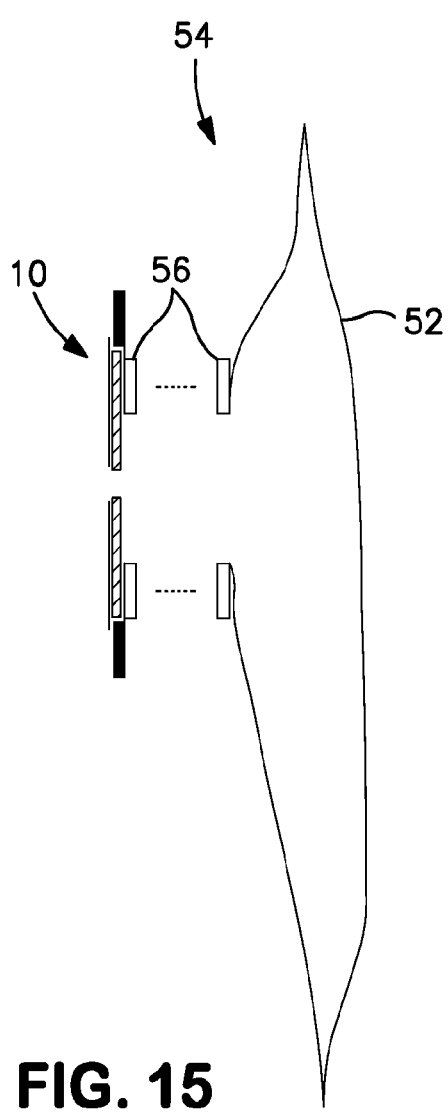
FIG. 15 is a schematic cross-sectional view showing $1^{st}$-$3^{rd}$ the embodiments used with a two-piece appliance.

The adhesive wafers 10 and release liners 20 described above may be used as a body fitment for any desired ostomy appliance. FIG. 14 illustrates a one-piece appliance 50 comprising a pouch 52 that is permanently attached to the adhesive wafer 10. The term "permanently attached" means that the pouch 52 and adhesive wafer 10 cannot easily be separated without risk of damage preventing the appliance 50 from continuing to be used. FIG. 15 illustrates a two-piece appliance 54 that additionally comprises a releasable ostomy coupling 56 between the adhesive wafer 10 and the pouch 52. The ostomy coupling 56 permits separation of the pouch 52, allowing the adhesive wafer 10 to remain in position on the body, and later re-fitting of the same, or a replacement, pouch 52. The ostomy coupling 56 may be a releaseable and/or resealable adhesive coupling, or it may be a mechanical coupling comprising interlocking or interference fit parts.

The ostomy pouch 52 is typically made of front and rear walls of flexible plastics film that is generally impermeable to liquid and gas. A suitable film includes, for example, a laminate of one or more layers of ethylene vinyl acetate (EVA), and one more layers of a gas barrier material, such as poly(vinylidene chloride) (PVDC). The walls and are welded together around a mutual periphery. The ostomy pouch 52 may further include one or more comfort layers lining the outer surface of one or both pouch walls to provide a soft, comfortable outer surface. The bottom of the pouch 52 may be sealed closed, or it may include a drainage aperture (not shown in FIGS. 14 and 15, but see FIG. 16) for drainage of the effluent collected in pouch 52.

In either a one-piece or two-piece appliance 50, 54, the provision of the release liner 20 of any of the preceding embodiments facilitates shaping of the moldable region 10a of the adhesive wafer 10, by manipulating the adhesive from the body-contacting side 16, and without the release liner 20 restraining moldability. In the case of a one-piece appliance 50, the pouch 52 obstructs access to the adhesive wafer 10 from the non-body-contacting side 18, normally making it difficult to shape the adhesive wafer 10. Access is only available from the body-contacting side 16, and normally considerable dexterity would be required to manipulate the adhesive without (i) the adhesive sticking to the finger and/or (ii) soiling the adhesive or the finger as a result of the contact. The use of the release liner 20 of the present invention can avoid, or at least mitigate, problems resulting from direct contact between the user's finger and the adhesive, making it much more straightforward to mold the adhesive.

Figure 16:
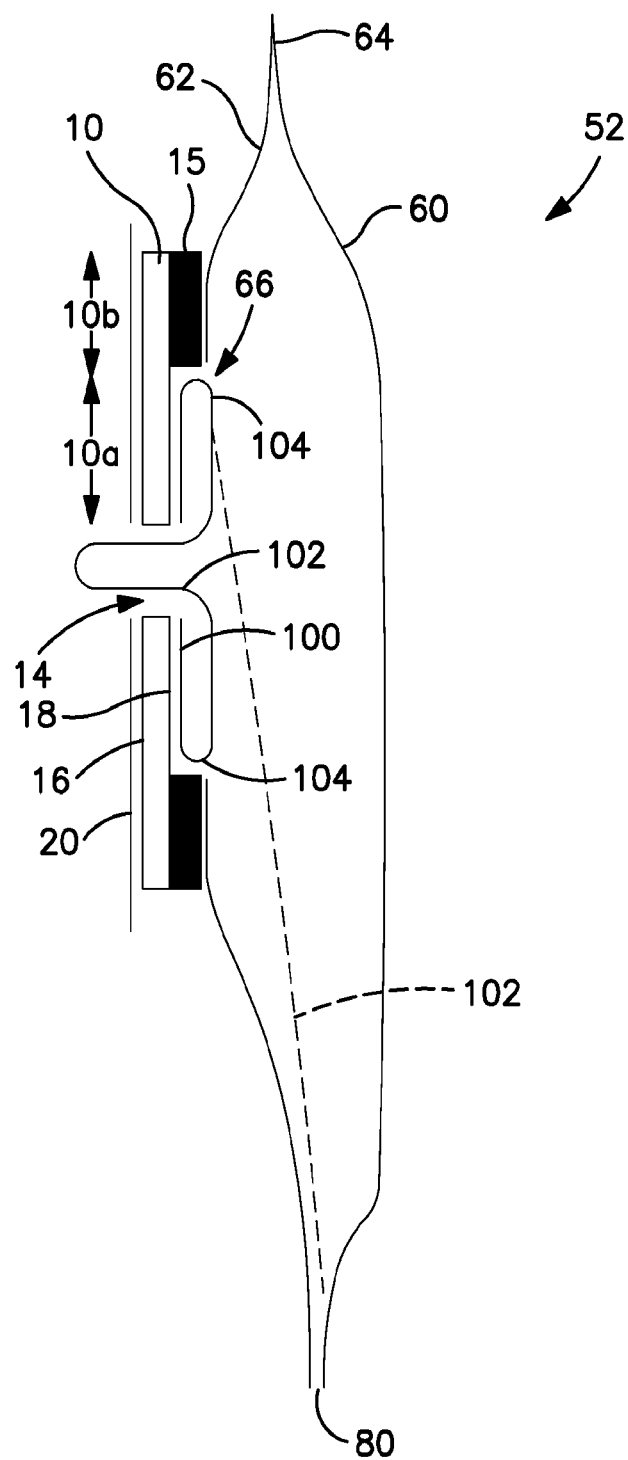
FIG. 16 is a schematic cross-sectional view showing a fourth embodiment in the form of a one-piece pouch appliance.

FIG. 16 illustrates a further embodiment in the form of a one-piece pouch appliance 50. The pouch 52 comprises a front wall 60 and rear wall 62 joined together along a peripheral seam 64, similarly to the pouch construction defined above. The rear wall 62 has an entrance aperture 66, around which is joined the adhesive wafer 10. The adhesive wafer 10 includes a moldable region 10a surrounding a stoma aperture 14 in the adhesive wafer 10. The moldable region 10a may optionally extend to the periphery of the entrance aperture 66 in the rear pouch wall 62. The boundary of the moldable region 10a may be defined by a backing 15, such as a foam piece that interfaces the adhesive wafer 10 to the pouch 52. In general, the boundary of the moldable region 10a of a one-piece appliance 50 occurs where the pouch 52 and wafer 10 are attached. The attachment may be accomplished by direct pouch to wafer contact or by communication through another component. The pouch 52 may have an optional drainage aperture 80, for example, formed by a discontinuity in the peripheral seam 64 at the bottom of the pouch 52.

The body-contacting face 16 of the adhesive wafer 10 is initially covered by a release liner 20. Preferably, the release liner 20 is as described in one of the previous embodiments, but any release liner 20 may be used as desired.

A feature of the present embodiment is that, in the moldable region 10a, the non-body-contacting face 18 of the adhesive wafer 10 is initially protected by an interior release liner 100. The release liner 100 prevents the non-body-contacting face 18 from adhering undesirably to the interior face of the front pouch wall 60. The release liner 100 comprises, or is coupled to, a grip portion 102 that permits the user to apply a force at least to separate the release liner 100 from the non-body-contacting face 18 of the wafer 10. The finger grip portion 102 is accessible through an aperture of the pouch 52, for example, through the starter hole 14 of the wafer 10, or through the drainage aperture 80 (if provided). In one form, the interior liner 100 is configured not just to be separable, but also to be removable from the pouch interior through the aperture by pulling on the finger grip portion 102. The finger grip portion 102 extends to project partly through the stomal aperture 14 (as shown in FIG. 16) or 80 (shown in phantom in FIG. 16), so that the finger grip portion 102 is accessible from outside the pouch 52.

The grip portion 102 is preferably attached to, or extends from, the release liner 100 via a fold or curve 104 extending away from the adhesive surface of the wafer 10. The fold 104 serves to enhance a peeling action when a force is applied to the grip portion 102. Instead of the force being applied in a direction to shear the release liner 100 from the adhesive surface, instead the force is applied via the fold 104 in a direction to at least partly lift the adhesive in a peeling action. Since the peeling separation force is usually significantly less than the shearing separation force, this not only reduces the stress within the release liner 100, but also enables a relatively small separation force to be applied, despite the release liner 100 being hidden from direct access and view.

In the form of FIG. 15, the grip portion 102 extends from an outer periphery of the release liner 100, such that the pulling on the grip portion 102 peels the release liner 100 from its outer periphery towards its inner periphery. The combination of the release liner 100 and its grip portion 102 has a sombrero-like shape, including a planar liner portion 100, a peripheral fold 104, and a re-entrant grip portion 102 that extends back towards the starter hole 14 and projects through the starter hole 14. The release liner 100 may include surface features that reduce surface contact with the adhesive. Such surface features include embossing, texturing to increase surface discontinuity. The release liner 100 is removed by twisting and/or pulling the tip of the grip portion 102 outside the pouch 52, preferably a combination of both. The pulling action peels and collapses the release liner 100 from its outer periphery towards the starter hole 14. The twisting action assists in bunching the release liner material to be withdrawn through the relatively small starter hole 14, as well as pulling on the release liner 100.

Figure 17:
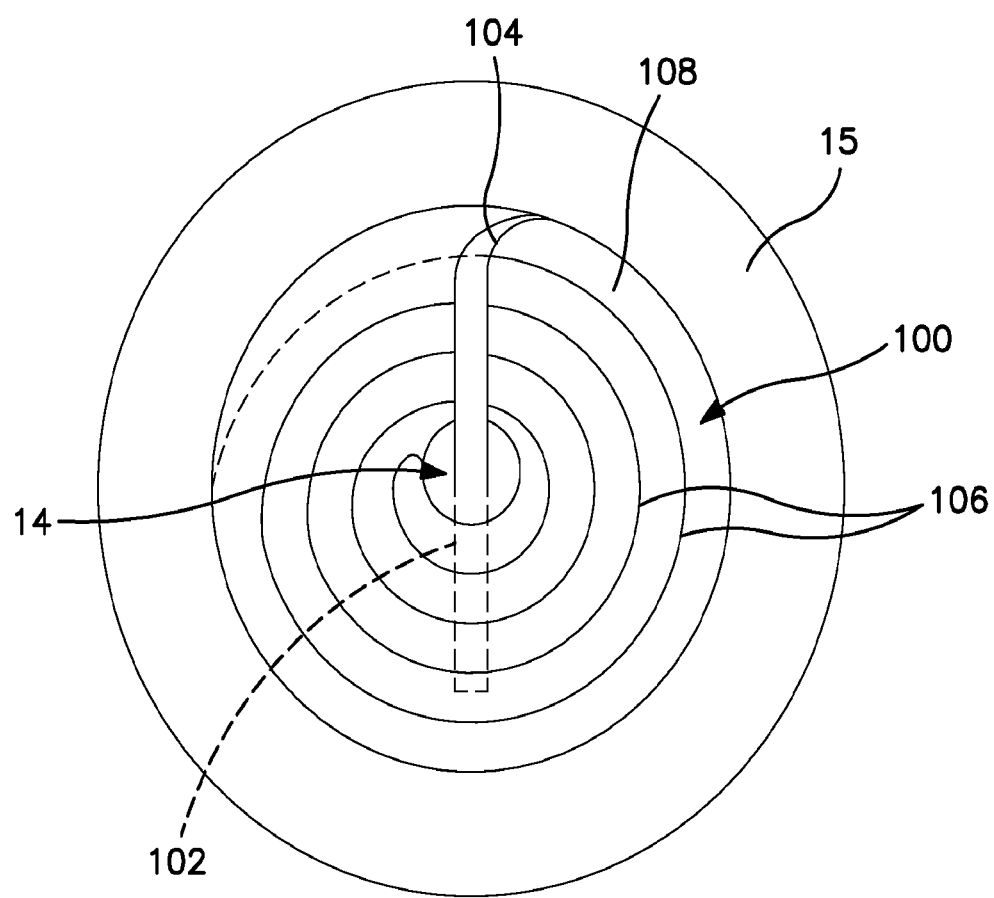
FIG. 17 is a schematic front view of the adhesive wafer from inside the pouch, showing a modification of the fourth embodiment.

In an alternative form of FIG. 17, the release liner 100 comprises at least one division line 106 that divides the release liner area 100 into one or more continuous and/or elongate segments, each connect to the, or a respective, grip portion 102. The segment preferably has a width less than the size of the starter hole 14, so that the segment can pass easily through the starter hole 14. As with the division line 30 in the release liner 20, the division line 106 may be a cut or slit through the release liner material, or it may be a line of weakness that may be torn. The line of weakness 106 may be defined by perforations, or by scoring or other material thinning, to define a frangible zone along which the material will tear when subjected to sufficient force.

Figure 7:
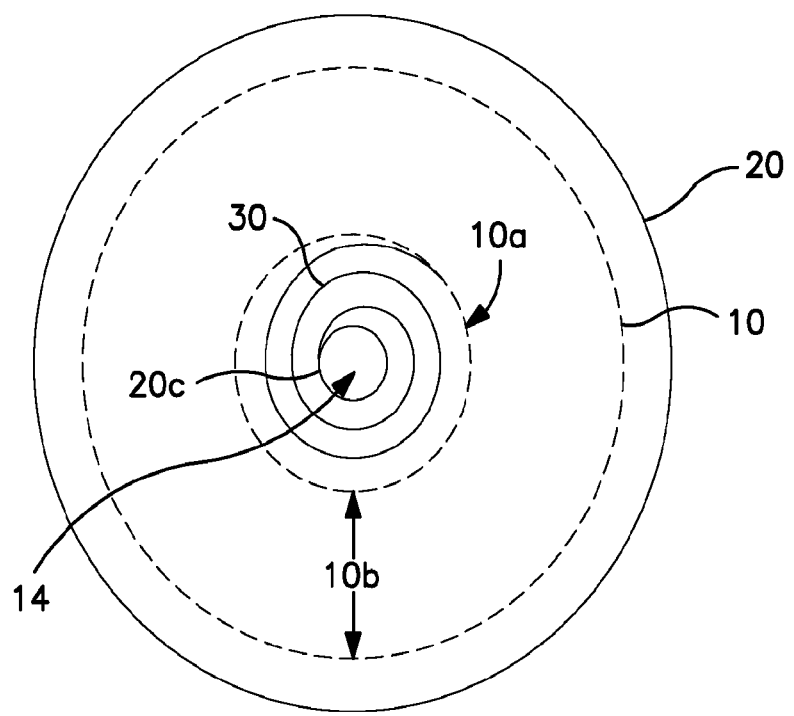
FIG. 7 is a schematic view similar to FIG. 3, showing a further modification of the second embodiment.
Figure 8:
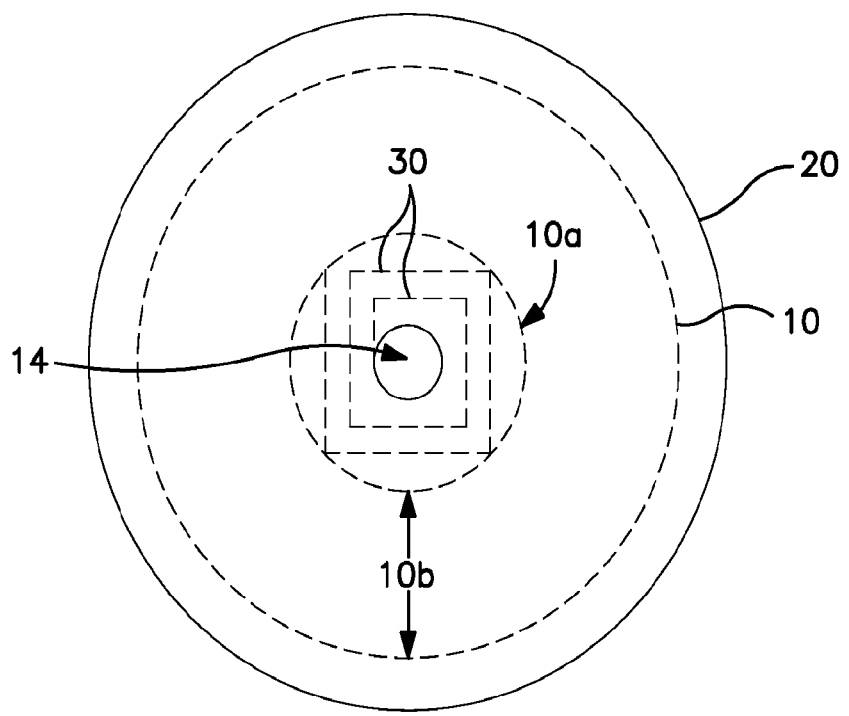
FIG. 8 is a schematic view similar to FIG. 3, showing a further modification of the second embodiment.
Figure 9:
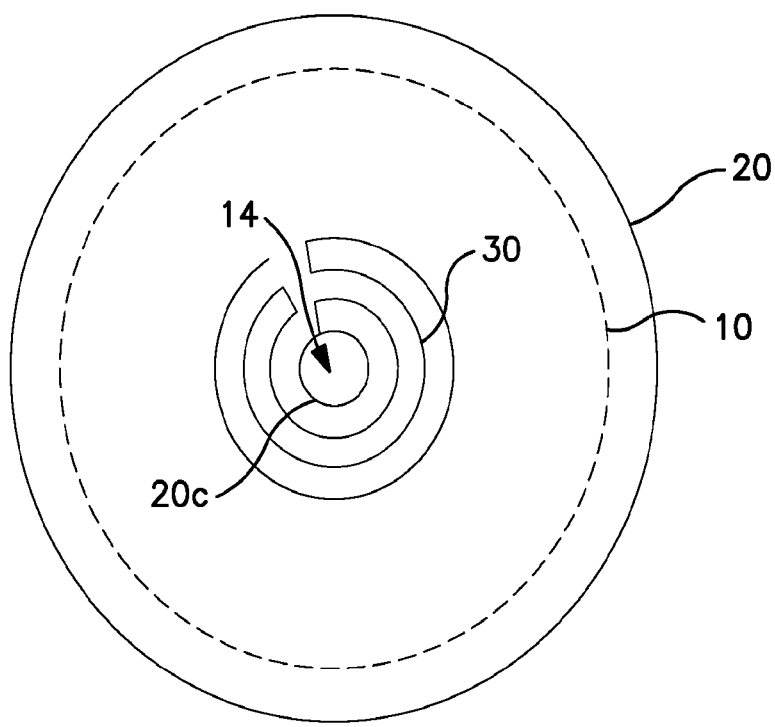
FIG. 9 is a schematic view similar to FIG. 3, showing a further modification of the second embodiment.

The division line 106 may have any suitable shape, a preferred example being a spiral, whether rounded or polygonal, or other spiral shape, and may be similar to the spirals of FIGS. 7 and 8. The divisional line 106 may alternatively include one or more boustrophedon turns to define, for example, a split spiral shape, similar to that of FIG. 9.

The grip portion 102 preferably extends from the outer periphery of the release liner 100 and/or spiral, and includes a fold 104. Pulling on the grip portion 102 gradually separates the segment. For example, the spiral shape unwinds inwardly. At the same time, the segment is withdrawn progressively through the starter hole.

Alternatively (not shown), the grip portion 102 may extend from the inner periphery of the release liner 100, preferably via the fold 104 to enhance peeling action when the grip portion 102 is pulled. Pulling on the grip portion 102 separates the segment, for example, by unwinding the spiral outwardly from the inner periphery, and the material is pulled out from the pouch interior via the starter hole 14.

Although the drawings illustrate only a single continuous segment defined by the division line 106, it will be appreciated that more than one segment may be defined and coupled to the same grip portion 102, or to respective different grip portions 102.

Figure 18:
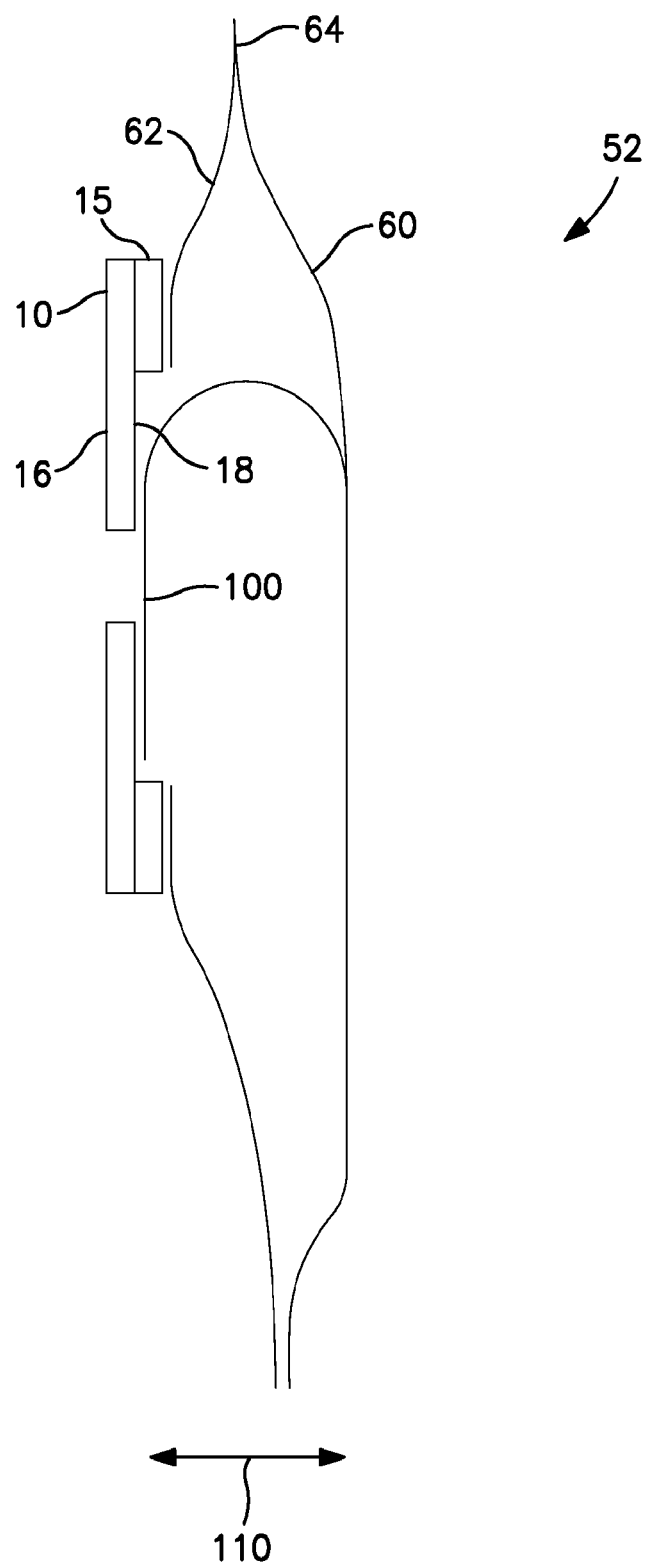
FIG. 18 is a schematic cross-sectional view showing a fifth embodiment in the form of a one-piece pouch appliance.
Figure 19:
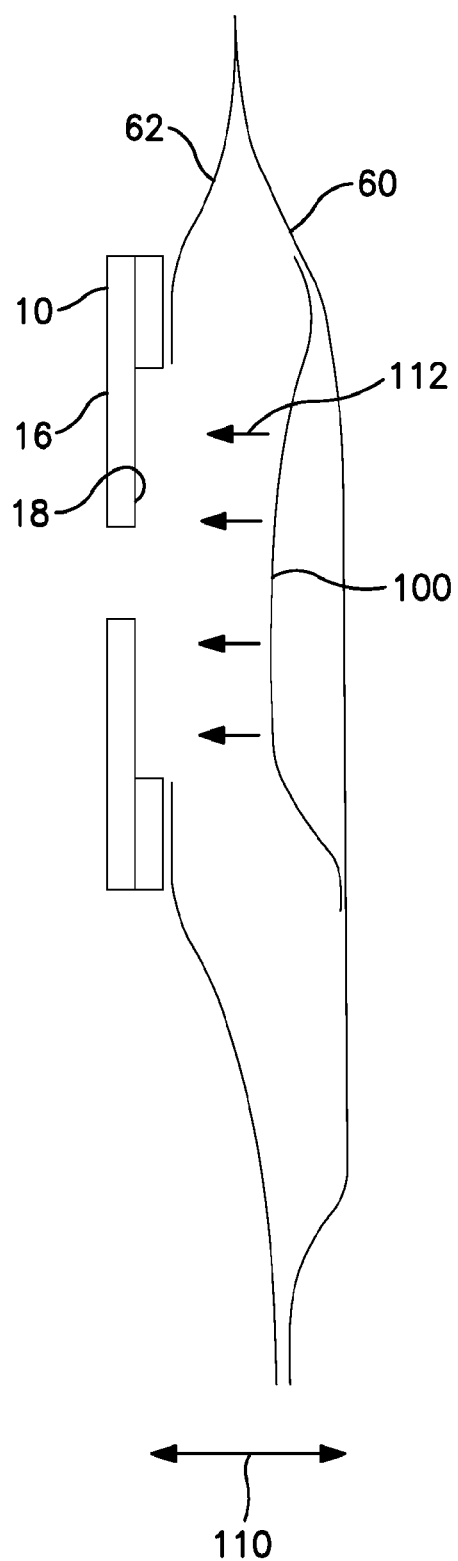
FIG. 19 is a schematic cross-sectional view similar to FIG. 18 but showing a modification of the fifth embodiment.

FIGS. 18 and 19 illustrate alternative forms of interior release liner 100 that are not withdrawn through the starter hole 14 but instead are attached to the interior face of the front pouch wall 60. The interior release liner 100 performs the same function in protecting the adhesive against accidental, unwanted adhesion against the front wall 60. In the form illustrated in FIG. 18, the interior release liner 100 is produced as part of the wafer laminate, and is attached (e.g., by adhesive or welding) to the front pouch wall 60 at a subsequent production step after, or during, formation of the pouch envelope. In use, pulling the pouch walls apart, as indicated by arrow 110, peels the interior release liner 100 from the non-body-contacting surface of the adhesive wafer 10, in order to permit molding, and FIG. 18 shows the release liner 100 beginning to peel from the non-body-contacting face 18. Once peeled, the release liner 100 may drop down into the collection volume of the pouch 52.

In the alternative form illustrated in FIG. 19, the interior release liner 100 is initially separate from the wafer 10, and is instead secured to the interior face of the front pouch wall 60. The release liner 100 may be slightly larger than the wafer 10, in order to accommodate production tolerances. During assembly of the pouch 52, or preparation for packaging, the front wall 60 is pressed towards the wafer 10, as indicated by arrows 112, thereby bringing the non-body-contacting face 18 of the wafer 10 into contact with the interior release liner 100 carried on the front pouch wall 60. In order to separate the interior release liner 100 in order to permit molding, the front and rear pouch walls 60, 62 are pulled apart, again as indicated by arrow 110.

A further advantage of having a release liner attached to the front pouch wall 60 is that the release characteristics also avoid any tendency of stomal effluent to stick to the front pouch wall 60 opposite the entrance aperture 62. The stomal effluent slides easily over the silicone coated sheet, to drop into the main collection volume of the pouch 52, leaving the entrance substantially unobstructed.

Figure 20:
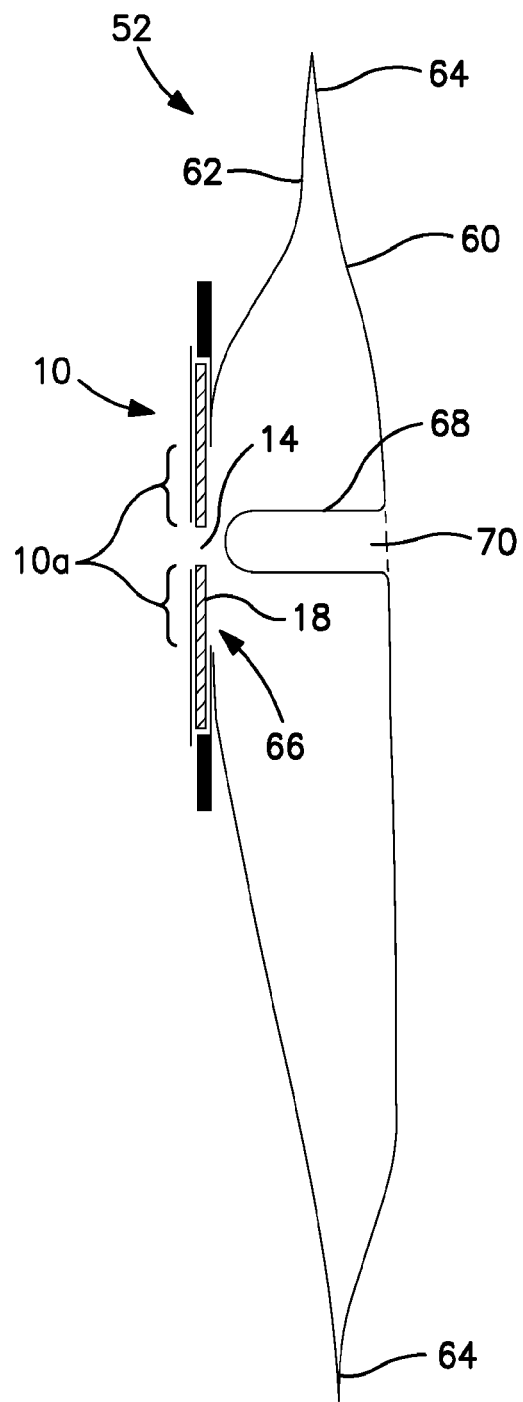
FIG. 20 is a schematic cross-sectional view showing a further embodiment of ostomy appliance including a pouch with a finger pocket.

FIG. 20 illustrates a further embodiment of ostomy appliance in the form of a pouch 52. The pouch 52 comprises a front wall 60 and a rear wall 62 joined together along a peripheral seam 64, similarly to the pouch construction described above. The rear wall 62 has an entrance aperture 66, around which is joined the adhesive wafer 10 for mounting the pouch 52 on the body. In this embodiment, the adhesive wafer 10 is joined permanently as a one-piece appliance (but it may alternatively be joined releasably by a coupling as a two-piece appliance). The adhesive wafer 10 includes a moldable region 10a surrounding a stomal aperture 14 in the adhesive wafer 10.

The pouch 52 further comprises a finger pocket 68 that extends from a mouth 70 at an exterior point or surface of the pouch 52 towards the entrance aperture 66 of the pouch 52 and/or towards the moldable region 10a of the adhesive wafer 10. The mouth 70 may be formed at any suitable point on the pouch 52, including, for example, the seam 64. However, in this embodiment, the mouth 70 is disposed in one of the pouch walls, for example, the front wall 60. The finger pocket 68 is made of flexible material, and is closed at its remote end, to preserve the integrity of the pouch 52. The finger pocket 68 may be made of the same material as the pouch wall 60. The finger pocket 68 may be formed by thermoforming a portion of the pouch wall 60, 62 into a pocket-like (or sock or sleeve) shape, or by attaching a separately formed pocket component at an aperture in the pouch wall 60, 62 corresponding to the mouth 70.

In a similar manner to the finger pocket 40 described earlier above, the finger pocket 68 facilitates molding of the moldable region 10a of the adhesive wafer 10, by enabling the adhesive to be manipulated through the flexible material of the finger pocket 68. Direct contact between the finger tip and the adhesive is avoided, and the user has the benefit of being able to access the adhesive from the non-body-contacting side 18, even though this face of the adhesive is obscured by the pouch 52. If desired, at least a portion of the front pouch wall 60 may be transparent to enable easier observation during molding of the adhesive.

While the finger pocket 68 of the last embodiment may be implemented independently of the release liners 20, 100 of the preceding embodiments, the last embodiment may optionally be combined with the release liners 20, 100 of these embodiments to further enhance protection and moldability of the adhesive wafer 10.

Figure 21:
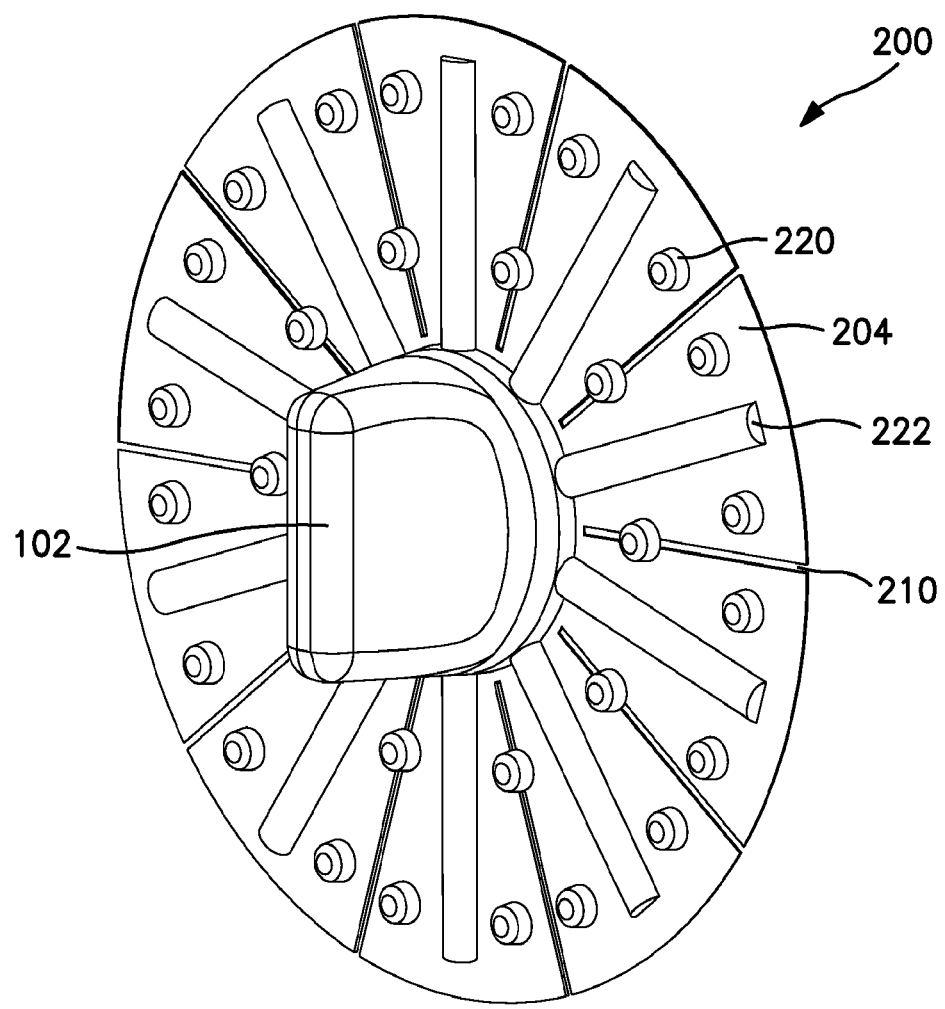
FIG. 21 is a schematic view of an embodiment of a release liner having a gripping portion.

FIG. 21 illustrates a release liner 200 having a finger gripping portion 202, an adhesive contacting surface 204 with projections 220, weakening lines 210 and stiffening ribs 222. The finger gripping portion 202 is digitally grippable for pulling of the release liner 200. The projections 220 provide discontinuities to the adhesive contacting surface so as to facilitate separation from the adhesive on the non-body contacting face 18 of the adhesive wafer 10. The weakening lines 210 permit folding of the release liner 200 to a shape allowing it to be easily removed through a starter hole 14 or other aperture. The stiffening ribs 222 provide support of the release liner segments 224.

Figure 22:
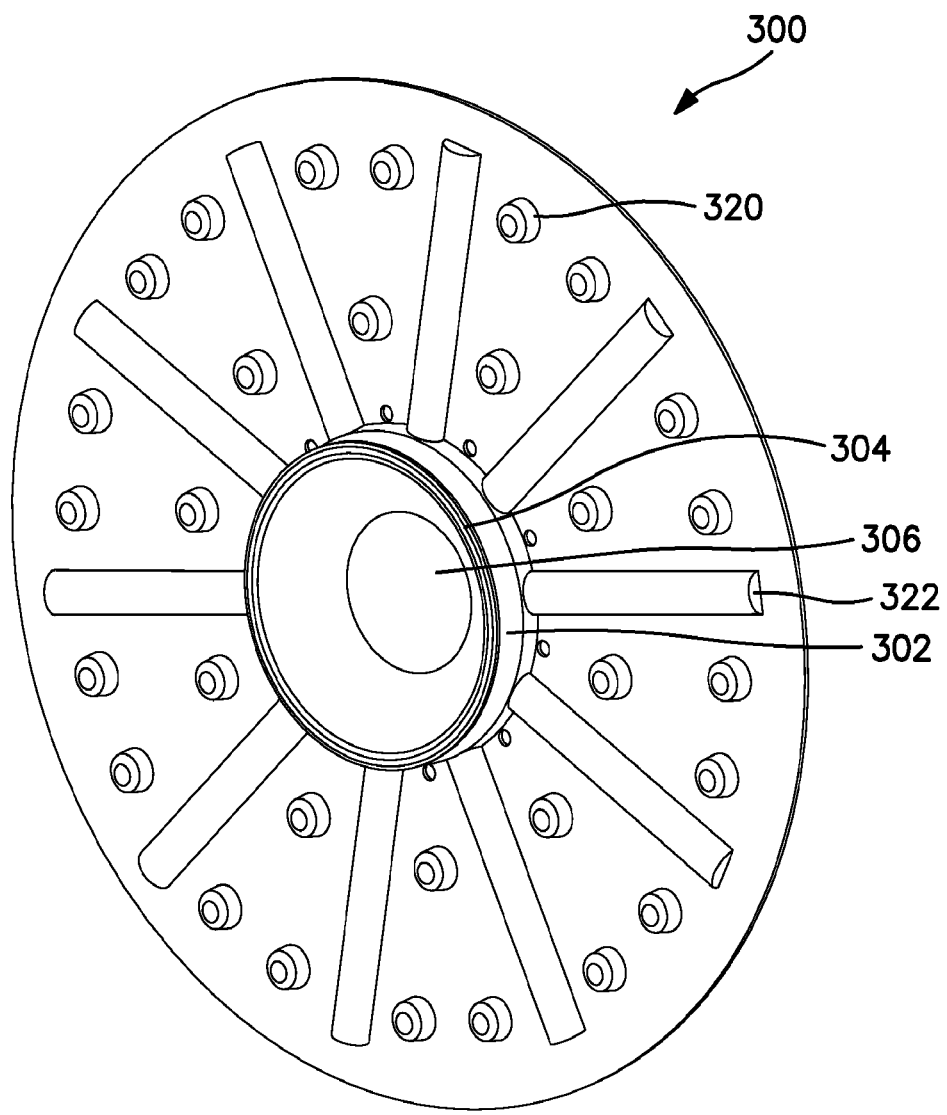
FIG. 22 is a schematic view of an embodiment of a release liner having a pushing portion.

FIG. 22 illustrates a release liner 300 having a pushing portion 302 and projections 320. The projections 320 are to facilitate separation of the release liner 300 from the adhesive on the non-body side contacting surface 18 of the adhesive wafer 10. The pushing portion 302 has a periphery 304 with dimensions that enable it to be retained in the starter hole 14 by friction. Other possible means of retention include adhesion and mechanical interference through interlocking or mating. This release liner 300 may be detached from the adhesive on the non-body side contacting surface of the adhesive wafer by being pushed into the pouch 52. The pushing portion 302 includes a recess 306 for receiving the tip of a finger tip to be inserted to push the release liner 300 and detach the release liner 300 from the adhesive of the non-body side contacting surface of the adhesive wafer. The release liner 300 may be partially or entirely dissolvable in the pouch contents. As shown, this release liner 300 includes stiffening ribs 322 for support. Weakening lines are not needed as this release liner 300 need not be folded for removal through the starter hole 14 or other aperture.

Any of the above embodiments may be combined as desired. A particularly preferred product includes both the external release liner 20 and the interior release liner 100 described above. In use, the interior release liner 100 is separated from the non-body-contacting face 18 to expose that adhesive face within the pouch 52. Next, if the external release liner 20 includes removable segments, an appropriate number of segments are removed, lifted, flexed or displaced to reduce restraint of the moldable region 10a. The moldable region 10a is then molded by hand, by folding or rolling the rim of the adhesive around the starter hole 14, so that the exposed non-body-contact surface 18 of the adhesive adheres to itself to anchor the moldable region 10a in the desired shape. Thereafter, the release liner 20, 100, 200, 300 (or what remains of the release liner 20, 100, 200, 300) is removed just prior to fitting to the peristomal skin. This design combines protection of both the interior and exterior adhesive surfaces with suitable release liners 20, 100, 200, 300, ease of removal of the release liners 20, 100, 200, 300, ease of molding without constraint by the release liners 20, 100, 200, 300, and ability to retain a release liner 20, 100, 200, 300 on the non-moldable region 10b of the adhesive to fully protect the adhesive surface until the appliance is ready to be adhered to the peristomal skin.

Many modifications and equivalents to the invention are possible without departing from the scope and/or principles of the invention as claimed.

We claim:

1. A one-piece ostomy appliance comprising an adhesive body fitment permanently attached to an ostomy pouch having an effluent receiving aperture for adhesively mounting the ostomy pouch to a wearer's body, the body fitment comprising:

an adhesive wafer for adhesively contacting the wearer's body peristomally, the adhesive wafer including a moldable region shapable by the user for allowing a user to manually mold a stomal aperture in said moldable region, and the adhesive wafer including, at least in the moldable region, an adhesive body-contacting face and an adhesive non-body-contacting face opposite the body-contacting face;

an interior release liner substantially covering said non-body-contacting face of the moldable region of the adhesive wafer, the interior release liner including a grip portion extending through the stomal aperture of the moldable region to enable gripping of the grip portion by a user's finger for enabling the interior release liner to be removed from said non-body-contacting face of the adhesive wafer, to facilitate molding of the moldable region.

2. The one-piece appliance of claim 1, wherein the stomal aperture is a starter hole within the moldable region of the adhesive wafer.

3. The one-piece appliance of claim 1, wherein the interior liner is configured to be removable by extracting the release liner from the appliance through the stomal aperture.

4. The one-piece appliance of claim 1, wherein the grip portion is configured to promote peeling of the interior release liner from the adhesive non-body-contacting face of the moldable region, when a pulling force is applied to the grip portion.

5. The one-piece appliance of claim 1, wherein the grip portion includes a fold to apply the pulling force in a direction to promote peeling.

6. The one-piece appliance of claim 1, wherein the grip portion extends from an inner or outer periphery of the interior release liner.

7. The one-piece appliance of claim 1, wherein the interior liner and the grip portion together have a sombrero-like shape.

8. The one-piece appliance of claim 1, wherein the interior liner comprises at least one division line dividing the release liner into one or more continuous segments that together define a shape making up the area of the release liner.

9. The one-piece appliance of claim 8, wherein the division line comprises one or more selected from: a cut; a slit; a line of weakening; a score; a line of perforations.

10. The one-piece appliance of claim 8, wherein the division line comprises one or more lines selected from: a spiral; a round spiral; a polygonal spiral; a split spiral with boustrophedon turns.

11. The one-piece appliance of claim 2, further comprising an exterior release liner covering the body-contacting face of the adhesive wafer.

\* \* \* \* \*